United States Patent
Katz et al.

(10) Patent No.: US 10,448,838 B2
(45) Date of Patent: Oct. 22, 2019

(54) ILLUSTRATING ERROR IN A TEMPERATURE DISTRIBUTION MAP

(71) Applicant: Biosense Webster (Israel) Ltd., Yokneam (IL)

(72) Inventors: Natan Sharon Katz, Atlit (IL); Lior Zar, Poria Illit (IL); Benjamin Cohen, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 775 days.

(21) Appl. No.: 14/886,910

(22) Filed: Oct. 19, 2015

(65) Prior Publication Data
US 2017/0105627 A1    Apr. 20, 2017

(51) Int. Cl.
*A61B 5/01* (2006.01)
*A61B 18/14* (2006.01)
(Continued)

(52) U.S. Cl.
CPC ............ *A61B 5/015* (2013.01); *A61B 5/7221* (2013.01); *A61B 5/7275* (2013.01); *A61B 5/743* (2013.01);
(Continued)

(58) Field of Classification Search
CPC ....... A61B 18/1492; A61B 5/01; A61B 5/015; A61B 2018/00357; A61B 2034/2051; A61B 5/7221
See application file for complete search history.

(56) References Cited

U.S. PATENT DOCUMENTS 6,067,371 A * 5/2000 Gouge .................. A61B 5/015
                                                                    374/E3.009
8,986,217 B2    3/2015 Boese et al.
(Continued)

FOREIGN PATENT DOCUMENTS

| EP | 2204133 A1 | 7/2010 |
|---|---|---|
| WO | WO 2008/110949 A1 | 9/2008 |
| WO | WO 2009/124301 A1 | 10/2009 |

OTHER PUBLICATIONS

European Search Report dated Mar. 10, 2017 from corresponding European Patent Application No. 16194397.2.

*Primary Examiner* — Patrick Fernandes
(74) *Attorney, Agent, or Firm* — Vincent J. Serrao

(57) ABSTRACT

A method, consisting of acquiring signals, indicative of temperatures at respective locations in a biological tissue, from a plurality of thermal sensors mounted on a probe in contact with the tissue, interpolating between the temperatures so as to produce a temperature distribution map, and displaying the temperature distribution map on a screen. The method also includes determining that at least one of the thermal sensors is a malfunctioning thermal sensor, and that remaining thermal sensors of the plurality are correctly operating. The at least one malfunctioning thermal sensor is assigned a first arbitrary temperature and the correctly operating thermal sensors are assigned second arbitrary temperatures. The method further includes interpolating between the first and second arbitrary temperatures so as to produce an error distribution map indicative of a suspect portion of the temperature distribution map, and superimposing graphically the error distribution map on the displayed temperature distribution map.

17 Claims, 9 Drawing Sheets

(51) Int. Cl.
    *G01K 15/00*     (2006.01)
    *A61B 5/00*     (2006.01)
    *G01K 13/00*     (2006.01)
    *A61B 18/00*     (2006.01)

(52) U.S. Cl.
    CPC ........ A61B 18/1492 (2013.01); G01K 13/002 (2013.01); G01K 15/007 (2013.01); *A61B 2018/00029* (2013.01); *A61B 2018/00357* (2013.01); *A61B 2018/00577* (2013.01); *A61B 2018/00797* (2013.01); *A61B 2218/002* (2013.01); *A61B 2560/0276* (2013.01); *G01K 2213/00* (2013.01)

(56) References Cited

U.S. PATENT DOCUMENTS

| | | | |
|---|---|---|---|
| 2006/0013281 A1* | 1/2006 | Sri-Jayantha | G06F 1/206 374/163 |
| 2009/0306650 A1 | 12/2009 | Govari et al. | |
| 2011/0130648 A1 | 6/2011 | Beeckler et al. | |
| 2014/0171821 A1 | 6/2014 | Govari et al. | |
| 2015/0112149 A1* | 4/2015 | Govari | A61B 5/743 600/301 |

\* cited by examiner

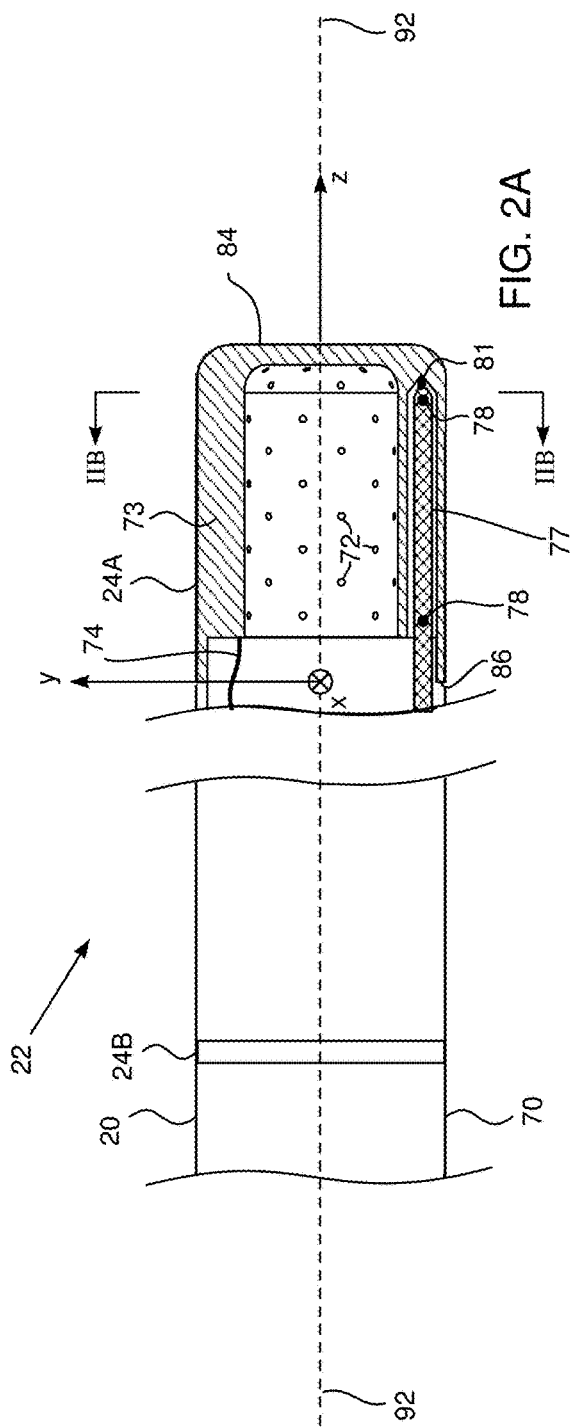
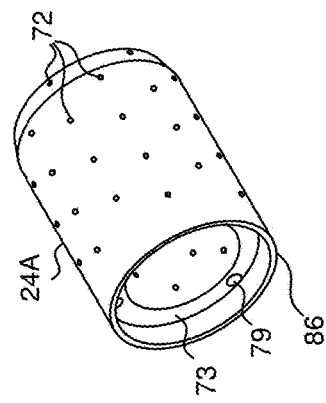
FIG. 2A
FIG. 2B
FIG. 2C

ILLUSTRATING ERROR IN A
TEMPERATURE DISTRIBUTION MAP

FIELD OF THE INVENTION

The present invention relates generally to distribution maps, and specifically to illustrating errors in maps of temperature distribution.

BACKGROUND OF THE INVENTION

It is advantageous to display information derived from measurements made during a surgical procedure graphically, so as to aid those performing the procedure to quickly comprehend the measurements. A number of prior art references address this subject. For example:

US Patent Application 2015/0112149, to Govari et al., whose disclosure is incorporated herein by reference, describes a method for displaying information, including receiving measurements, with respect to an invasive probe inside a body of a subject, of probe parameters consisting of a force exerted by the probe on tissue of the subject and temperatures measured by sensors of the probe.

U.S. Pat. No. 8,986,217 to Boese et al., whose disclosure is incorporated herein by reference, describes a mapping catheter for determination of data of an area of an organ embodied as a flat surface, especially of the heart. The data is to be presented graphically, with at least one thermosensor essentially aligned in the direction of the longitudinal axis of the mapping catheter.

US Patent Application 2014/0171821, to Govari et al., whose disclosure is incorporated herein by reference, describes a medical probe that includes an insertion tube having a distal end configured for insertion into a body of a patient. A plurality of temperature sensors are mounted within a conductive cap of the probe, and the disclosure states that the temperature readings of the sensors can be combined and interpolated to give a map of temperature over the area of the probe tip.

Documents incorporated by reference in the present patent application are to be considered an integral part of the application except that, to the extent that any terms are defined in these incorporated documents in a manner that conflicts with definitions made explicitly or implicitly in the present specification, only the definitions in the present specification should be considered.

SUMMARY OF THE INVENTION

An embodiment of the present invention provides a method, including:

acquiring signals, indicative of temperatures at respective locations in a biological tissue, from a plurality of thermal sensors mounted on a probe in contact with the tissue;

interpolating between the temperatures so as to produce a temperature distribution map;

displaying the temperature distribution map on a screen;

determining that at least one of the thermal sensors is a malfunctioning thermal sensor, and that remaining thermal sensors of the plurality are correctly operating;

assigning the at least one malfunctioning thermal sensor a first arbitrary temperature and the correctly operating thermal sensors second arbitrary temperatures;

interpolating between the first and second arbitrary temperatures so as to produce an error distribution map indicative of a suspect portion of the temperature distribution map; and superimposing graphically the error distribution map on the displayed temperature distribution map.

Typically, interpolating between the temperatures includes using a predetermined method of interpolation and extrapolation, and interpolating between the first and second arbitrary temperatures includes using the predetermined method of interpolation and extrapolation.

Alternatively, interpolating between the temperatures includes using a first predetermined method of interpolation and extrapolation, and interpolating between the first and second arbitrary temperatures includes using a second predetermined method of interpolation and extrapolation, different from the first predetermined method.

In a disclosed embodiment the error distribution map includes a region enclosed by an isotherm generated by the interpolating between the first and second arbitrary temperatures.

In a further disclosed embodiment the error distribution map is at least partially transparent so that a region of the temperature distribution map underlying the error distribution map is visible.

In a yet further disclosed embodiment the error distribution map is differentiated visually from the temperature distribution map.

Typically the error distribution map is a subset of the temperature distribution map.

In an alternative embodiment the biological tissue consists of a myocardium, and the signals are acquired during ablation of the myocardium.

In a further alternative embodiment determining that the at least one of the thermal sensors is the malfunctioning thermal sensor consists of registering that a temperature indicated by the at least one of the thermal sensors is outside a preset acceptable range of temperatures.

In a yet further alternative embodiment the error distribution map and the displayed temperature distribution map are two dimensional maps. Alternatively, the error distribution map and the displayed temperature distribution map are three dimensional maps.

There is further provided, according to an embodiment of the present invention embodiment, apparatus, including:

a probe, in contact with a biological tissue and having a plurality of thermal sensors; and a processor configured to:

acquire signals, indicative of temperatures at respective locations in the biological tissue, from the plurality of thermal sensors, interpolate between the temperatures so as to produce a temperature distribution map, display the temperature distribution map on a screen.

determine that at least one of the thermal sensors is a malfunctioning thermal sensor, and that remaining thermal sensors of the plurality are correctly operating, assign the at least one malfunctioning thermal sensor a first arbitrary temperature and the correctly operating thermal sensors second arbitrary temperatures, interpolate between the first and second arbitrary temperatures so as to produce an error distribution map indicative of a suspect portion of the temperature distribution map, and superimpose graphically the error distribution map on the displayed temperature distribution map.

There is further provided, according to an embodiment of the present invention, a method, including:

acquiring signals, indicative of respective metrics at respective locations in a biological tissue, from at least one sensor mounted on a probe in proximity with the tissue;

interpolating between the metrics so as to produce a metric distribution map;

displaying the metric distribution map on a screen;

determining that at least one of the signals is indicative of an incorrect metric value, and that remaining signals are indicative of correct metric values;

assigning the at least one of the signals a first arbitrary metric value and the remaining signals second arbitrary metric values;

interpolating between the first and second arbitrary metric values so as to produce an error distribution map indicative of a suspect portion of the metric distribution map; and superimposing graphically the error distribution map on the displayed metric distribution map.

In a disclosed embodiment the biological tissue includes a heart, and the metric includes a local activation time of the heart.

The error distribution map and the metric distribution map may be three-dimensional maps.

In a further disclosed embodiment the incorrect metric value conflicts with an expected metric value determined in response to the correct metric values.

In a yet further disclosed embodiment the at least one of the signals provides insufficient information for determining a correct metric value.

The present disclosure will be more fully understood from the following detailed description of the embodiments thereof, taken together with the drawings, in which:

BRIEF DESCRIPTION OF THE DRAWINGS

FIGS. 2A, 2B, and 2C schematically illustrate a distal end of a probe, according to an embodiment of the present invention;

DETAILED DESCRIPTION OF EMBODIMENTS

Overview

Figure 1:
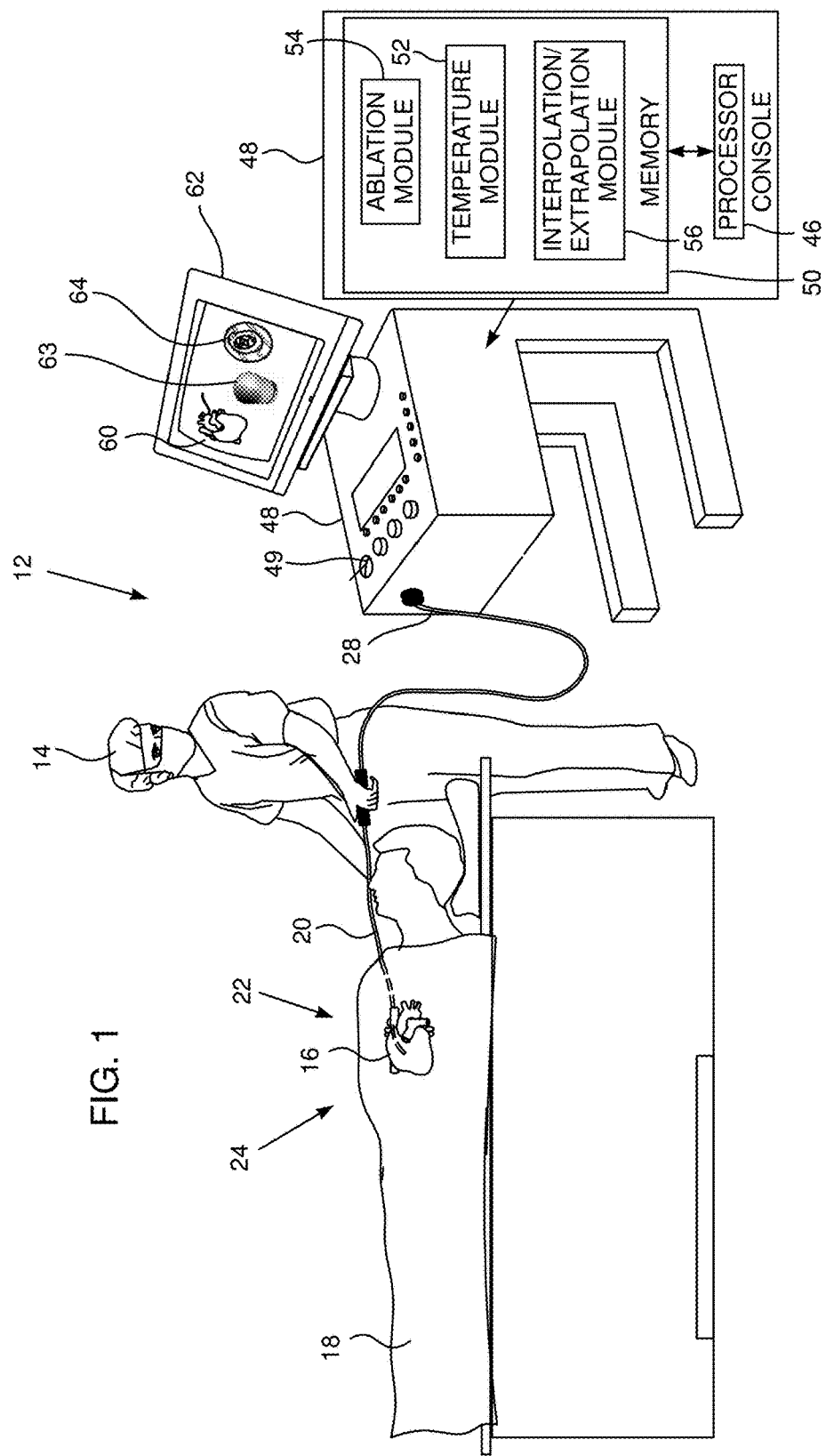
FIG. 1 is a schematic illustration of an invasive medical procedure, according to an embodiment of the present invention.

In an invasive surgical procedure a catheter or probe with multiple thermal sensors at the distal tip may be used to generate a temperature distribution map for the vicinity of the tip. In prior art systems, if one or more of the sensors malfunctions, such a malfunction may be notified, for example by lighting a warning light, but the map is not altered to indicate the malfunction.

Embodiments of the present invention provide a remedy if this problem occurs during a procedure, by incorporating a "suspect region" into the distribution map. Initially, signals, indicative of temperatures at respective locations in a biological tissue, are acquired from a plurality of thermal sensors mounted on a probe in contact with the tissue. A temperature distribution map is formed by interpolating and extrapolating between the temperatures, and the map is displayed on a screen.

At some stage in the procedure it is determined that at least one of the thermal sensors is a malfunctioning thermal sensor, while the remaining thermal sensors of the plurality are correctly operating. (The determination may be made, for example, by finding that the malfunctioning sensor gives a reading outside an acceptable range of readings.) The at least one malfunctioning thermal sensor is assigned a first arbitrary temperature and the correctly operating thermal sensors are assigned second arbitrary temperatures.

An error distribution map, indicative of a suspect portion of the temperature distribution map, is generated by interpolating and extrapolating between the arbitrary temperatures. Typically the error distribution map comprises a region within a preset isotherm of a map produced from the interpolation and extrapolation of the arbitrary temperatures. The error distribution map is superimposed graphically on the displayed temperature distribution map, and the superimposed region acts to indicate a possible problem area of the temperature distribution map.

System Description

In the following description, like elements in the drawings are identified by like numerals, and the like elements are differentiated as necessary by appending a letter to the identifying numeral.

FIG. 1 is a schematic illustration of an invasive medical procedure using apparatus 12, according to an embodiment of the present invention. The procedure is performed by a medical professional 14, and, by way of example, the procedure in the description hereinbelow is assumed to comprise ablation of a portion of a myocardium 16 of the heart of a human patient 18. However, it will be understood that embodiments of the present invention are not just applicable to this specific procedure, and may include substantially any procedure on biological tissue.

In order to perform the ablation, professional 14 inserts a probe 20 into a lumen of the patient, so that a distal end 22 of the probe enters the heart of the patient. Distal end 22 comprises electrodes 24 mounted on the outside of the distal end, the electrodes contacting respective locations of the myocardium. Probe 20 has a proximal end 28. Distal end 22 of the probe is described in more detail below with reference to FIGS. 2A, 2B and 2C.

Apparatus 12 is controlled by a system processor 46, which is located in an operating console 48 of the apparatus. Console 48 comprises controls 49 which are used by professional 14 to communicate with the processor. During the procedure, processor 46 typically tracks a location and an orientation of distal end 22 of the probe, using any method known in the art. For example, processor 46 may use a magnetic tracking method, wherein magnetic transmitters external to patient 18 generate signals in coils positioned in the distal end. The Carto® system produced by Biosense Webster, of Diamond Bar, Calif., uses such a tracking method.

The software for processor 46 may be downloaded to the processor in electronic form, over a network, for example. Alternatively or additionally, the software may be provided on non-transitory tangible media, such as optical, magnetic, or electronic storage media. The track of distal end 22 is typically displayed on a three-dimensional representation 60 of the heart of patient 18 on a screen 62.

In order to operate apparatus 12, processor 46 communicates with a memory 50, which has a number of modules used by the processor to operate the apparatus. Thus, memory 50 comprises a temperature module 52, an ablation module 54, and an interpolation/extrapolation module 56, the functions of which are described below. Memory 50 typically comprises other modules, such as a force module for measuring the force on end 22, a tracking module for operating the tracking method used by processor 46, and an irrigation module allowing the processor to control irrigation provided for distal end 22. For simplicity, such other modules, which may comprise hardware as well as software elements, are not illustrated in FIG. 1.

Processor 46 uses results of measurements of temperature acquired by module 52 to display on screen 62 a temperature distribution map 63 and/or a temperature distribution map 64. Maps 63 and 64 are described in more detail below.

FIGS. 2A, 2B, and 2C schematically illustrate distal end 22 of probe 20, according to an embodiment of the present invention. FIG. 2A is a sectional view along the length of the probe, FIG. 2B is a cross-sectional view along a cut IIB-IIB that is marked in FIG. 2A, and FIG. 2C is a perspective view of a section of the distal end. An insertion tube 70 extends along the length of the probe and is connected at the termination of its distal end to a conductive cap electrode 24A, which is assumed herein to be used for ablation. FIG. 2C is a schematic perspective view of cap electrode 24A. Cap electrode 24A has an approximately plane conducting surface 84 at its distal end and a substantially circular edge 86 at its proximal end. Conductive cap electrode 24A is herein also termed the ablation electrode. Proximal to ablation electrode 24A there are typically other electrodes such as an electrode 24B. Typically, insertion tube 70 comprises a flexible, biocompatible polymer, while electrodes 24A, 24B comprise a biocompatible metal, such as gold or platinum, for example. Ablation electrode 24A is typically perforated by an array of irrigation apertures 72.

An electrical conductor 74 conveys radio-frequency (RF) electrical energy from ablation module 54 (FIG. 1), through insertion tube 70, to electrode 24A, and thus energizes the electrode to ablate myocardial tissue with which the electrode is in contact. Module 54 controls the level of RF power dissipated via electrode 24A. During the ablation procedure, cooling fluid flowing out through apertures 72 may irrigate the tissue under treatment.

Temperature sensors 78 are mounted within conductive cap electrode 24A at locations that are arrayed around the distal tip of the probe, both axially and circumferentially. In this example, cap 24A contains six sensors, with one group of three sensors in a distal location, close to the tip, and another group of three sensors in a slightly more proximal location. This distribution is shown only by way of example, however, and greater or smaller numbers of sensors may be mounted in any suitable locations within the cap. Sensors 78 may comprise thermocouples, thermistors, or any other suitable type of miniature temperature sensor. Sensors 78 are connected by leads (not shown in the diagram) running through the length of insertion tube 70 to provide temperature signals to temperature module 52.

In a disclosed embodiment cap 24A comprises a side wall 73 that is relatively thick, on the order of 0.5 mm thick, in order to provide the desired thermal insulation between temperature sensors 78 and the cooling fluid inside a central cavity 75 of the tip. The cooling fluid exits cavity 75 through apertures 72. Sensors 78 are mounted on rods 77, which are fitted into longitudinal bores 79 in side wall 73. Rods 77 may comprise a suitable plastic material, such as polyimide, and may be held in place at their distal ends by a suitable glue 81, such as epoxy. U.S. patent application Ser. No. 13/716,578, which is incorporated herein by reference, describes a catheter having temperature sensors mounted in a similar configuration to that described above. The arrangement described above provides an array of six sensors 78, but other arrangements, and other numbers of sensors, will be apparent to those having ordinary skill in the art, and all such arrangements and numbers are included within the scope of the present invention.

In the description herein, distal end 22 is assumed to define a set of xyz orthogonal axes, where an axis 92 of the distal end corresponds to the z axis of the set. For simplicity and by way of example, the y axis is assumed to be in the plane of the paper, the xy plane is herein assumed to correspond to the plane defined by circle 86, and the origin of the xyz axes is assumed to be the center of the circle.

Typically, distal end 22 contains other functional components, which are outside the scope of the present disclosure and are therefore omitted for the sake of simplicity. For example, the distal end of the probe may contain steering wires, as well as sensors of other types, such as a position sensor and a force sensor. Probes containing components of these kinds are described, for example, in U.S. Patent Applications 2009/0306650 and 2011/0130648, which are incorporated herein by reference.

Figure 3A:
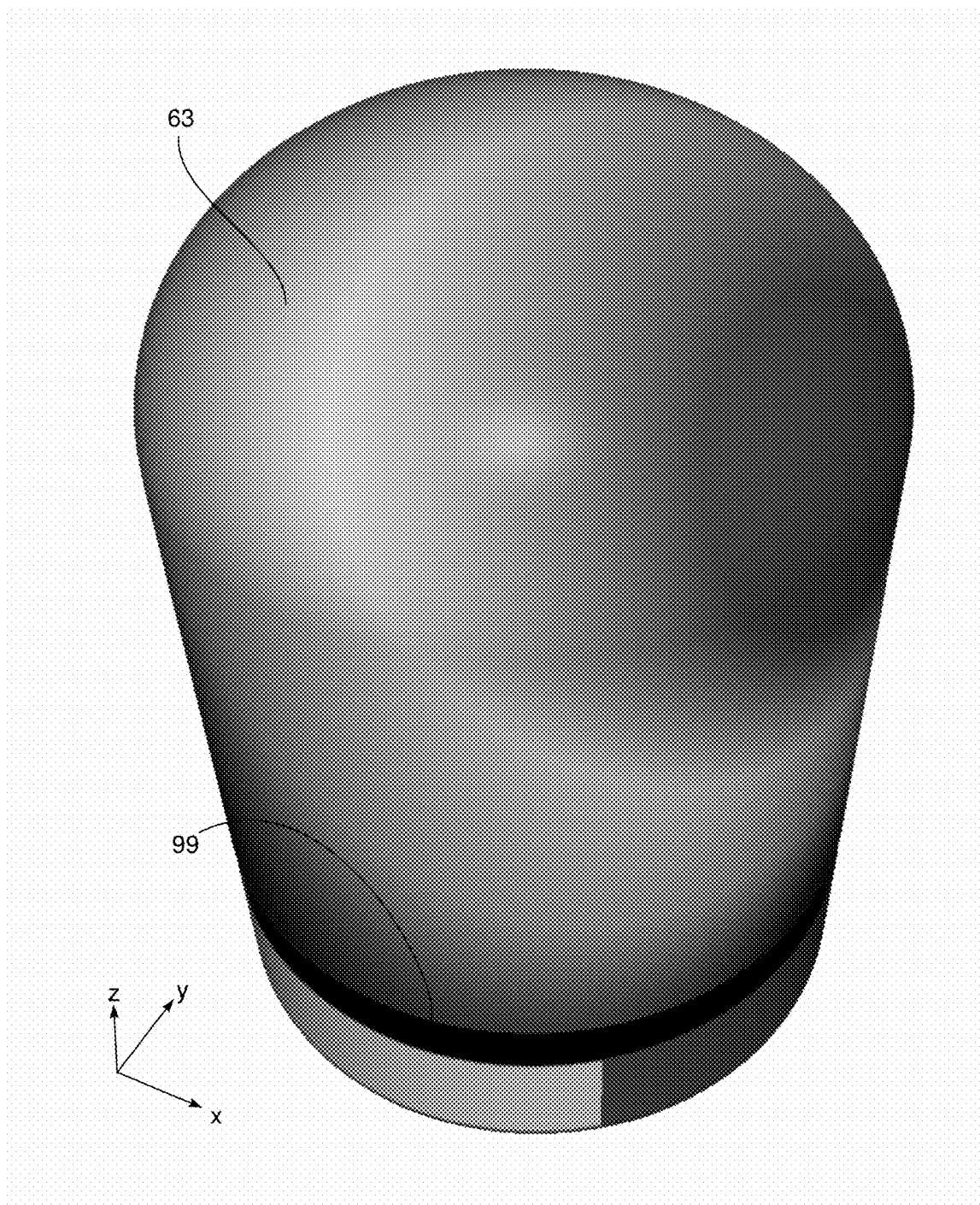
FIGS. 3A and 3B are schematic diagrams illustrating the spatial distribution of temperature in the vicinity of the distal end, according to an embodiment of the present invention.
Figure 3B:
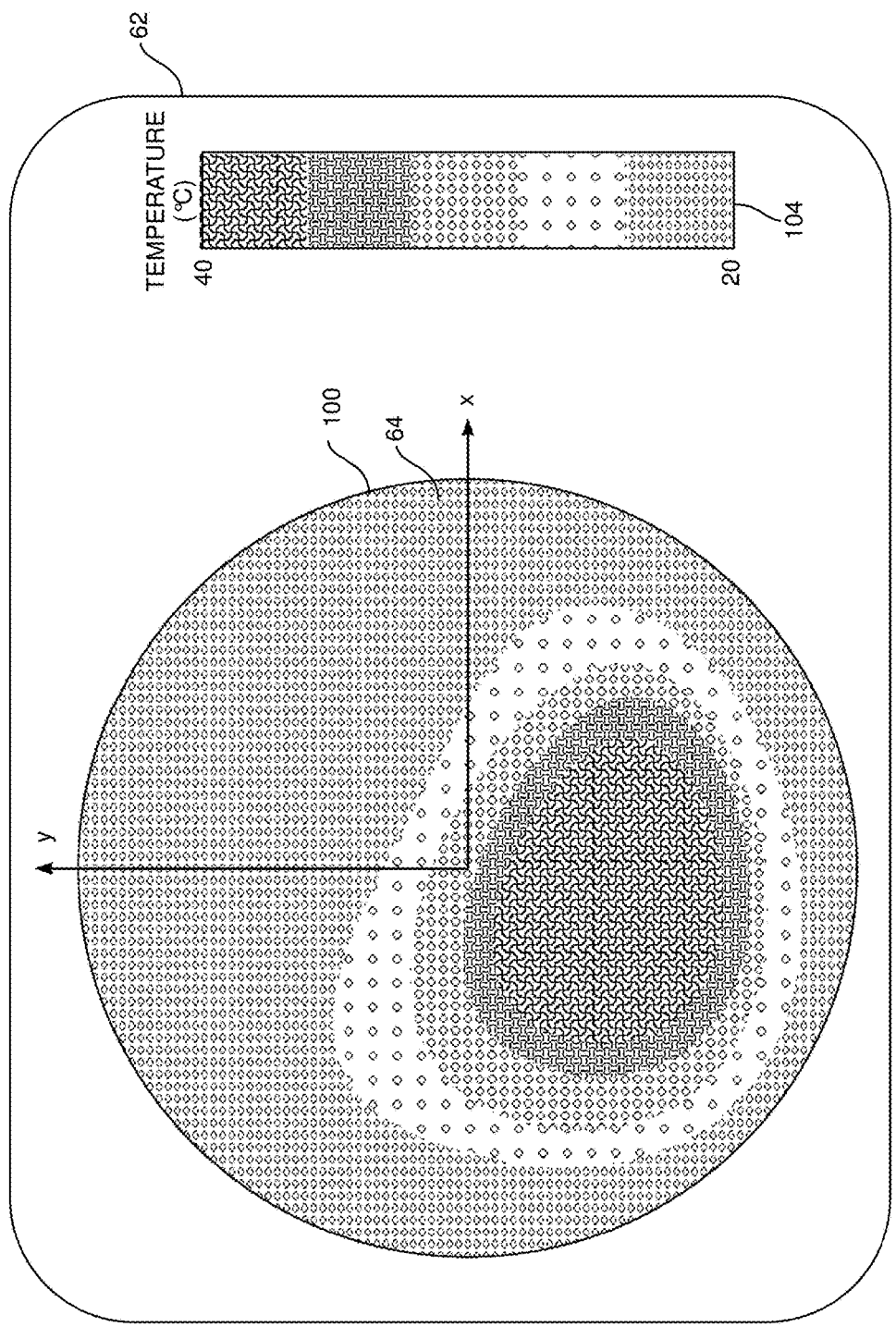

FIGS. 3A and 3B are schematic diagrams illustrating, in different presentations, the three-dimensional (3D) spatial distribution of temperature in the vicinity of distal end 22, according to an embodiment of the present invention. FIG. 3A illustrates the spatial distribution as 3D map 63, and FIG. 3B illustrates the spatial distribution as two-dimensional (2D) map 64. Using measurements provided by temperature sensors 78, as well as knowledge of the locations of the sensors with respect to each other and with respect to the xyz axes of distal end 22, processor 46 uses temperature module 52 to generate a 3D spatial distribution of the temperatures of the external surface of electrode 24A. The spatial distribution may be presented on screen 62 as 3D map 63. Alternatively or additionally, the processor may project the 3D spatial distribution to a 2D graphical representation of the distribution, corresponding to 2D map 64. The processor may present either or both maps on screen 62. Both maps are assumed to be drawn with respect to the xyz axes defined above for distal end 22.

The projection from a 3D distribution to a 2D distribution may be by any method known in the projection arts. The calculation of the distribution, from measurements of sensors 78 and from knowledge of the sensor positions, may use any method of interpolation and extrapolation from the measurements that is known in the art. Suitable methods are the Inverse Distance Weighting method, and the Gaussian process regression or Kriging method. In an embodiment of the present invention interpolation/extrapolation module 56 (FIG. 1) comprises at least one such method, and the module is accessed by processor 46 as required.

3D map 63 is a perspective map, and an edge 99 of the map corresponds to edge 86 of electrode 24A. 2D map 64 is drawn as a circular map on screen 62, a bounding circle 100 of the map corresponding with edge 86 of electrode 24A. For map 64, x and y axes are shown in FIG. 3B, the axes corresponding to the axes defined above for distal end 22 and being assumed, by way of example, to be parallel to the edges of screen 62. The axes for either map may be displayed on screen 62, and indications of other elements of the distal end, such as the locations of sensors 78, may be shown on the screen to assist professional 14 in relating the orientation of the maps to the orientation of the distal end.

3D map 63 and 2D map 64 are typically color maps showing the different temperatures of the external surface of electrode 24A, and a legend 104 (FIG. 3B) may be displayed with the maps showing values of the temperatures for the different colors. It will be understood that in the maps any specific color is typically enclosed by isothermal lines, or isotherms, which are usually not shown in the map. (In the figures different colors are schematically illustrated by different shadings or different gray scales.) In some embodiments the numerical values measured by each of sensors 78 may also be displayed on map 63 and/or map 64. For simplicity, the display of such numerical values is not illustrated in FIGS. 3A and 3B.

In a disclosed embodiment, prior to interpolation and extrapolation, the temperatures measured by sensors are normalized. An expected coldest temperature measured by the sensors may be set as 0, and an expected hottest temperature measured by the sensors may be set as 1. The expected coldest temperature may be the lowest value displayed on legend 104, and the expected hottest temperature may be the highest value displayed on the legend. By way of example the expected coldest temperature may be 20° C. and the expected hottest temperature may be 40° C., as is illustrated in FIG. 3B. It will be understood that, in the case of map 63 or map 64 being a color map, while the map may be prepared using normalized values for the temperatures, the colors of the map indicate non-normalized temperature values.

Figure 4:
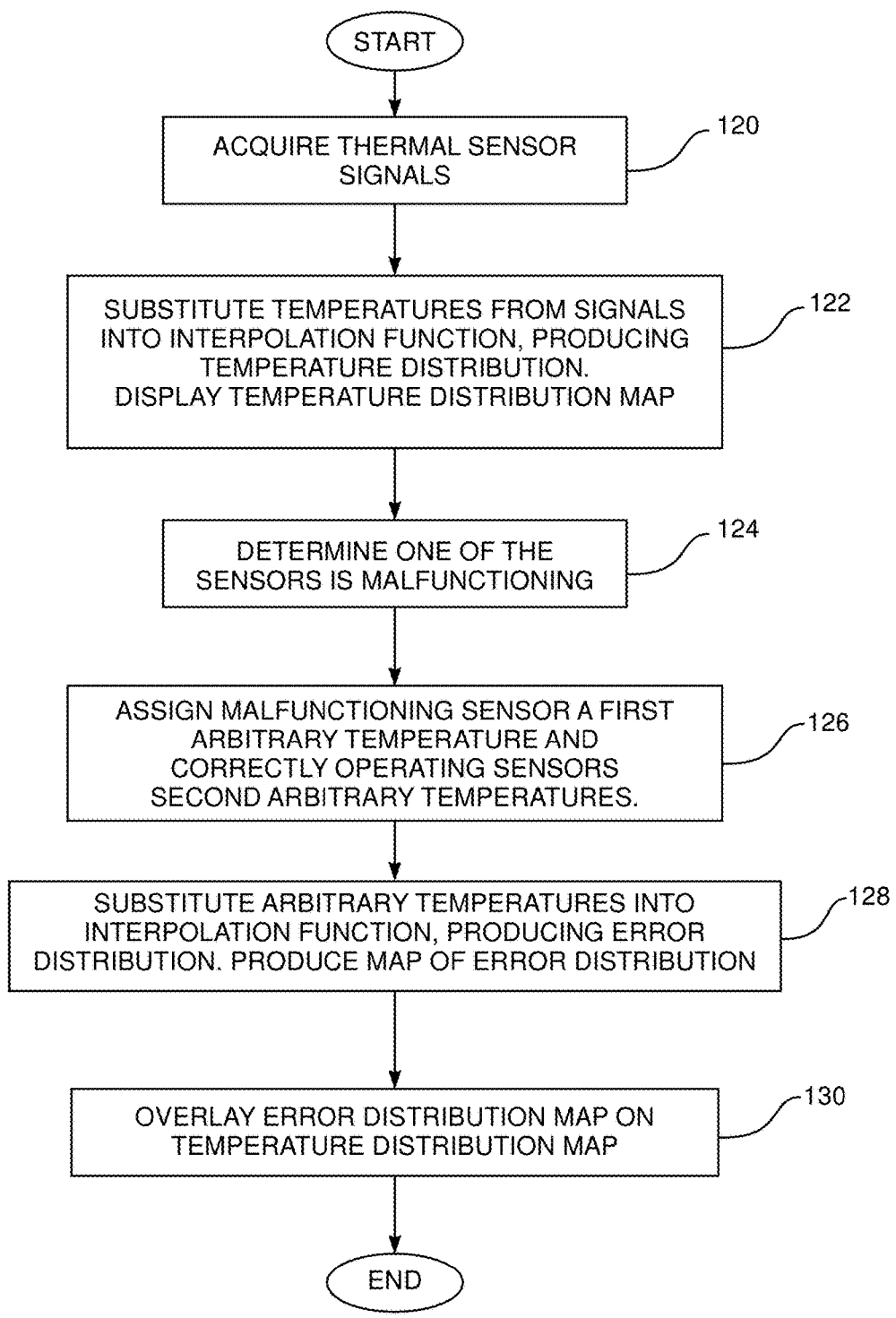
FIG. 4 is a flowchart of steps followed by a processor, according to an embodiment of the present invention.

FIG. 4 is a flowchart of steps followed by processor 46 in operating apparatus 12, according to an embodiment of the present invention. In an initial step 120 processor 46 acquires signals from sensors 78, and uses temperature module 52 to convert the acquired signal levels to temperatures. By way of example, in the following description, except where otherwise stated, processor 46 is assumed not to have normalized the temperature values produced by module 52 as described above. In addition, module 56 is assumed to store the Inverse Distance Weighting method. However, those having ordinary skill in the art will be able to adapt the description, mutatis mutandis, for embodiments where the temperatures are normalized, and/or where a different method of interpolation and extrapolation is stored in module 56.

In a first interpolation and display step 122, the processor accesses interpolation/extrapolation module 56, and applies the method stored in the module to interpolate and extrapolate between the temperatures of sensors 78, according to the spatial positions of the sensors. The method produces a 3D spatial distribution of temperatures. The processor may present the spatial distribution as a 3D temperature distribution map on screen 62, and/or project the 3D spatial distribution to a 2D temperature distribution map which is displayed on the screen. FIGS. 3A and 3B illustrate typical 3D and 2D maps produced in step 122.

In a malfunctioning sensor step 124, the processor determines that one of sensors 78 is malfunctioning. The determination is typically made by the processor registering that the sensor gives a temperature reading outside a preset acceptable range of temperatures. The malfunction may be caused, for example, by a broken lead to or from the sensor, by a short-circuit in one of the leads, or by failure of the sensor itself. In some embodiments professional 14 suspects that one of sensors 78 is malfunctioning, and uses controls 49 to inform the processor of the suspect sensor, whereupon the processor proceeds as described below in step 126.

In an assignment step 126, the processor assigns the malfunctioning sensor a first arbitrary temperature, and the remaining, correctly operating sensors, a second arbitrary temperature. In one embodiment the first arbitrary temperature is set at 0° C., and the second arbitrary temperature is set at 100° C. If the processor is using a normalized system, then these settings are equivalent to the first arbitrary normalized temperature being set as 0, and the second arbitrary normalized temperature being set as 1.

In a second interpolation and display step 128, the processor accesses interpolation/extrapolation module 56. The processor typically applies the method stored in the module to interpolate and extrapolate between the first arbitrary temperature of the malfunctioning sensor and the second arbitrary temperature of the correctly operating sensors, according to the spatial positions of the sensors. Alternatively, the processor may use a different method to perform the interpolation and extrapolation. The interpolation and extrapolation produces a 3D spatial distribution of temperatures, based on the arbitrary temperatures, and herein termed a 3D spatial arbitrary temperature distribution.

The interpolation producing the 3D spatial arbitrary temperature distribution typically generates a continuous distribution of temperatures between the first arbitrary and second arbitrary temperatures. (The extrapolation typically produces a continuous distribution of temperatures outside the two arbitrary temperatures.) In an embodiment of the present invention, a section of the 3D arbitrary temperature distribution that is suspected to have erroneous results is selected, and is herein termed an error region.

In a disclosed embodiment the selected section comprises a portion of the 3D spatial arbitrary temperature distribution that is contained within a preset isotherm of the distribution. A 2D or 3D error distribution map may be used to illustrate areas, in the respective 2D or 3D map produced in step 122, corresponding to the error region.

Thus, referring back to 2D arbitrary temperature distribution map 64 (FIG. 3B), the 2D selected section is a 2D area in the map that may be displayed on screen 62, and an expression for the 2D selected section is given by expression (1):

$$\{(x,y)|(x^2+y^2) \leq r^2 \text{ and } T \geq K\} \qquad (1)$$

where r is the radius of bounding circle 100,

T is the temperature of a point (x,y) within the bounding circle, and

K is a value of the preset isotherm.

It will be understood from expression (1) that the selected 2D section, the 2D error distribution map of the error region, is a subset of map 64. Similarly, in the case of the 3D arbitrary temperature distribution, the 3D selected section— the 3D error distribution map of the error region—is a subset of map 63.

For the example above where the first arbitrary temperature is 0° C., and the second arbitrary temperature is 100° C., the isotherm may, by way of example, be preset at 60° C., so that in expression (1) K=60. In the case where temperatures are normalized, then this example is equivalent to the first and second arbitrary normalized temperatures respectively being 0 and 1, and K being 0.6.

Figure 5A:
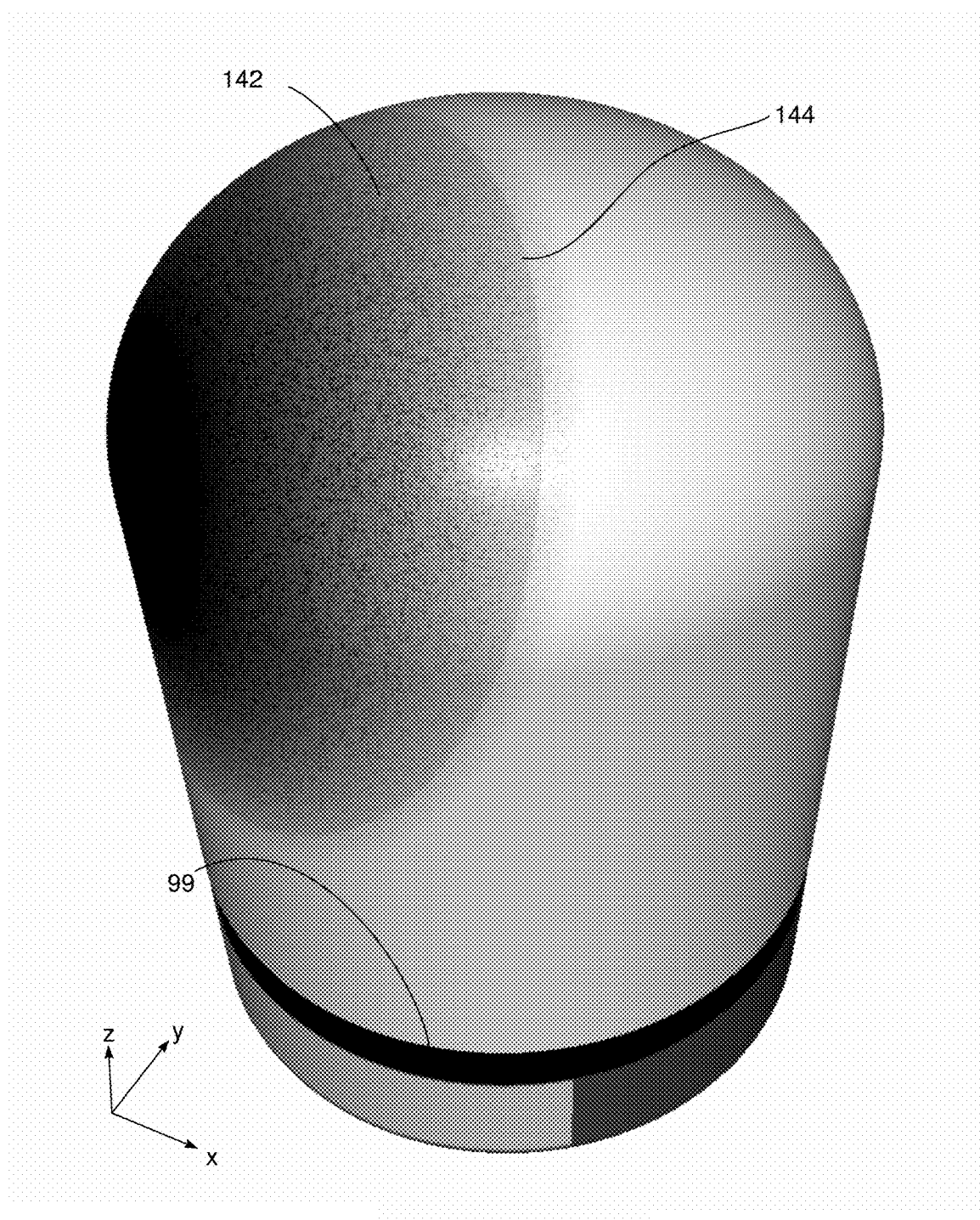
FIGS. 5A and 5B schematically illustrate a 3D and a 2D error distribution map, according to an embodiment of the present invention.
Figure 5B:
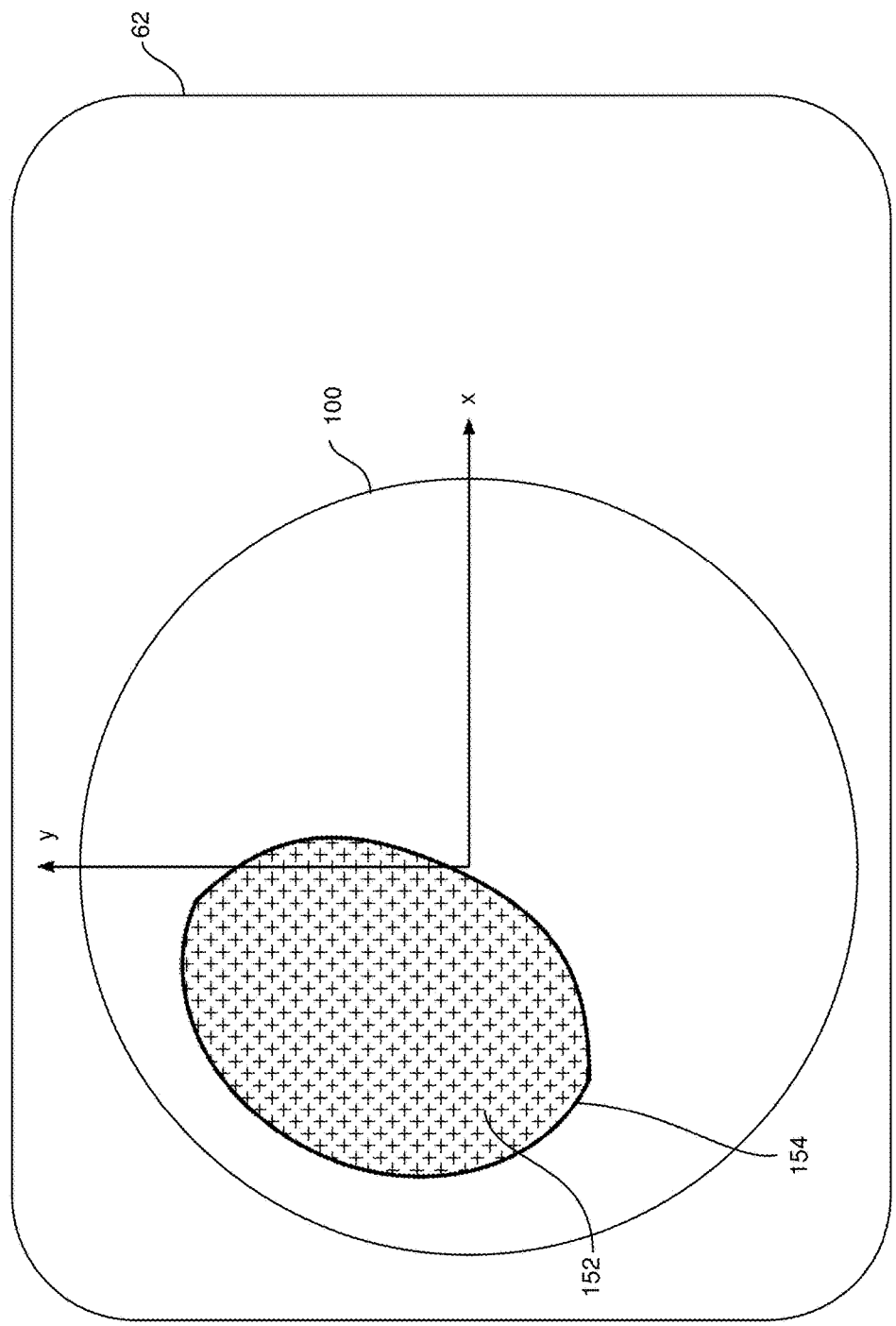

FIGS. 5A and 5B respectively schematically illustrate a 3D error distribution map 142 and a 2D error distribution map 152, according to an embodiment of the present invention. Maps 142 and 152 are produced using the exemplary arbitrary temperature values given above, i.e., where the first arbitrary temperature is 0° C., and the second arbitrary temperature is 100° C. 3D map 142 is drawn using the same perspective as map 63 and illustrates edge 99. 2D map 152 is drawn within bounding circle 100. An isotherm 144 of 3D map 142, corresponding to the edge of the error region, is by way of example preset at T=60° C. An isotherm 154 of 2D map 152 is also set at T=60° C. Thus, K=60 in expression (1).

Returning to the flowchart of FIG. 4, in a final step 130, the processor overlays, i.e., superimposes graphically, the error distribution map generated in step 128 on the temperature distribution map of step 122.

Figure 6A:
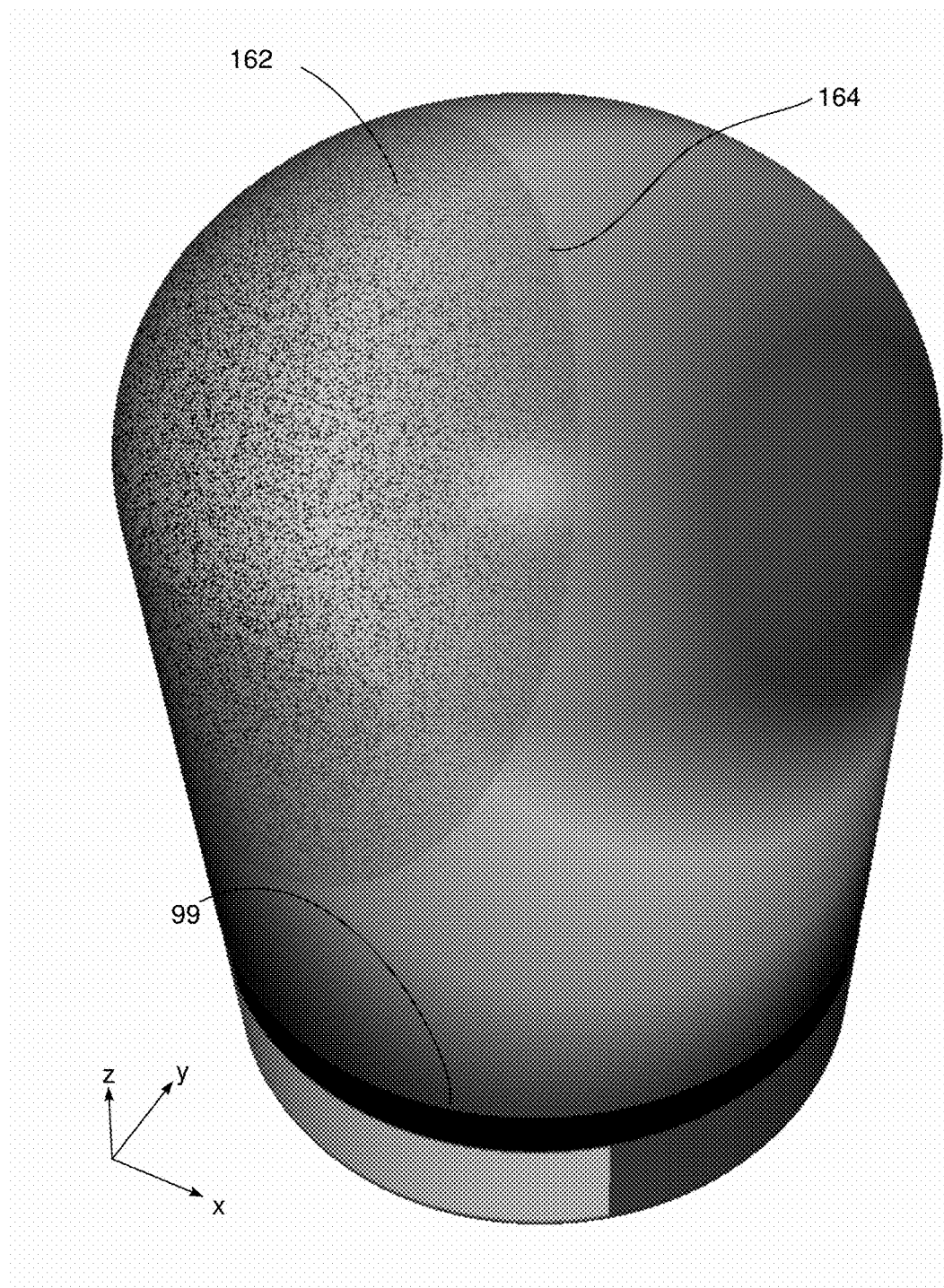
FIGS. 6A and 6B schematically illustrate an implementation of the flowchart of FIG. 4, according to an embodiment of the present invention.
Figure 6B:
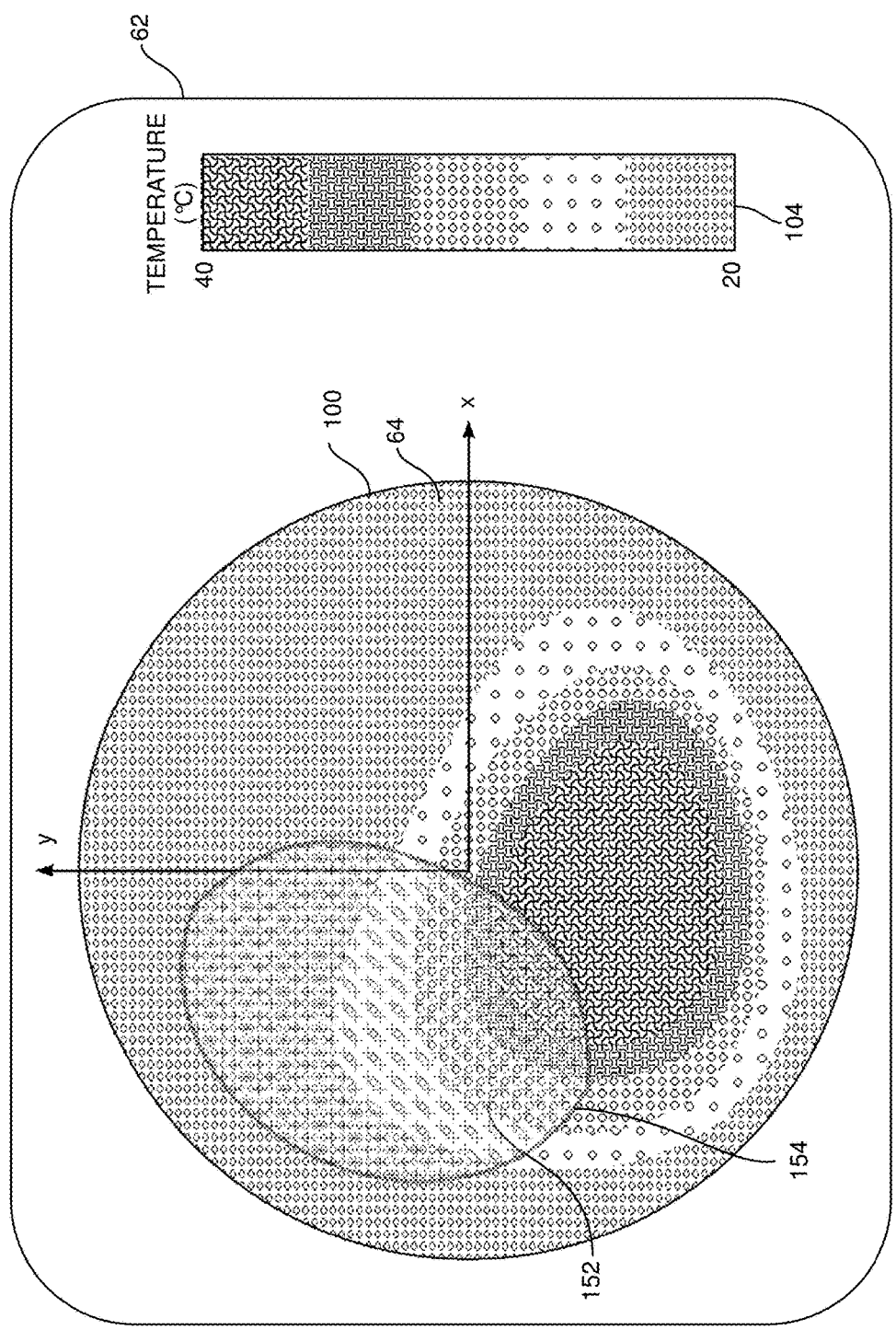

FIGS. 6A and 6B schematically illustrate an implementation of the flowchart of FIG. 4, according to an embodiment of the present invention. For a two-dimensional representation, the flowchart is assumed to be applied to 2D temperature distribution map 64 of FIG. 3B, and is also assumed to generate 2D error distribution map 152 of FIG. 5B, so that line 154 represents isotherm T=K=60, and a region, within the isotherm, represents the 2D error distribution map. For a three-dimensional representation, the flowchart is assumed to be applied to 3D temperature distribution map 63 of FIG. 3A, and is also assumed to generate error distribution map 142 of FIG. 5A, so that line 144 represents isotherm T=60, and a region, within the isotherm, represents the 3D error distribution map.

In the implementation of the flowchart, i.e., when step 130 has completed, error distribution maps 142 and 152 are implemented to be visually different and distinct from the elements of maps 63 and 64, and in one embodiment maps 142 and 152 are presented on screen 62 as black elements within a white background. However, the error distribution maps, generated by the flowchart, may be presented on screen 62 by any convenient method that differentiates them visually from their underlying temperature distribution maps. In one embodiment maps 142 and 152 are implemented to be at least partially transparent, so that temperature values of maps 63 and 64, underlying maps 142 and 152 and so being suspect, are visible. In an alternative embodiment, maps 142 and 152 comprise isotherms, of values greater than the bounding isotherm corresponding to lines 144 and 154, which are drawn as at least partially transparent black lines. The thickness of the normalized isotherm lines may increase as the value of the isotherm increases.

The description above provides one example of how an error distribution map may be superimposed on another distribution map, so as to provide an indication of a suspect portion of the other map. It will be understood that the methods described above may be applied, mutatis mutandis, to other systems where there may be a suspect portion in a distribution map.

For example, prior to the ablation described above (with reference to FIG. 1) professional 14 may use processor 46 to prepare a 3D local activation time (LAT) distribution map of the heart. Such a 3D distribution map is usually generated from LAT measurements made by electrodes 24 acquiring signals from the heart at known points, and interpolating and extrapolating between these points, typically using one of the methods referenced above.

Processor 46 may be used to analyze data used to generate the graph, and may determine that an area of the graph may be suspect, typically by finding that there are insufficient points for valid interpolation or extrapolation. In this case, to generate a 3D error distribution map one or more signals from points in proximity to the area may be assigned a first arbitrary metric value, and the remaining signals may be assigned a second arbitrary metric value. The values may be normalized, so that the first normalized value is set at 0, and the second normalized value is set at 1. Using normalized or non-normalized arbitrary values, processor 46 produces a 3D error distribution map, generally as described above. The processor then superimposes the 3D error map on the 3D LAT distribution map.

As an alternative example, one or more of the signals acquired for the LAT measurements may conflict with other measurements. The conflicting measurements are typically from one or more points in proximity to points where the LAT measurement is correct. For example, there may be a larger than acceptable LAT difference between the points generating the conflict and points in proximity to these points. To generate a 3D error distribution map the one or more signals giving conflicting LAT values may be assigned a first arbitrary metric value, and the remaining signals may be assigned a second arbitrary metric value. The values may be normalized, so that the first normalized value is set at 0, and the second normalized value is set at 1.

As described above, using normalized or non-normalized arbitrary values, processor produces a 3D error distribution map. The processor then superimposes the 3D error map on the 3D LAT distribution map.

It will be appreciated that there are other cases where a 2D or 3D error distribution map may be determined and respectively overlaid on a 2D or 3D distribution map of a metric, using the methods described above, and all such cases are assumed to be comprised within the scope of the present invention.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. A computer implemented method, comprising:
  acquiring signals, indicative of temperatures at respective locations in a biological tissue, from a plurality of thermal sensors mounted on a probe in contact with the biological tissue; and
  performing, by a processor, the steps of:
    interpolating between temperatures determined from the signals so as to produce a temperature distribution map;
    displaying the temperature distribution map on a screen;
    determining that there is at least one malfunctioning thermal sensor of the plurality of thermal sensors, and that remaining thermal sensors of the plurality of thermal sensors are correctly operating thermal sensors;
    assigning the at least one malfunctioning thermal sensor a first arbitrary temperature and each of the correctly operating thermal sensors a second arbitrary temperature;
    interpolating between the first and second arbitrary temperatures so as to produce an error distribution map indicative of an error region of the temperature distribution map; and
    superimposing graphically the error distribution map on the temperature distribution map displayed on the screen so as to indicate the error region on the screen during a procedure for treating the biological tissue with the probe.

2. The method according to claim 1, wherein interpolating between the temperatures comprises using a predetermined method of interpolation, and wherein interpolating between the first and second arbitrary temperatures comprises using the predetermined method of interpolation.

3. The method according to claim 1, wherein interpolating between the temperatures comprises using a first predetermined method of interpolation, and wherein interpolating between the first and second arbitrary temperatures comprises using a second predetermined method of interpolation, different from the first predetermined method.

4. The method according to claim 1, wherein the error distribution map comprises a region enclosed by an isotherm generated by the interpolating between the first and second arbitrary temperatures.

5. The method according to claim 1, wherein the error distribution map is at least partially transparent so that the error region of the temperature distribution map underlying the error distribution map is visible.

6. The method according to claim 1, wherein the error distribution map is differentiated visually from the temperature distribution map.

7. The method according to claim 1, wherein the error distribution map is a subset of the temperature distribution map.

8. The method according to claim 1, wherein acquiring signals includes acquiring signals during ablation of a myocardium.

9. The method according to claim 1, wherein determining that the at least one of the thermal sensors is the malfunctioning thermal sensor comprises registering that a temperature indicated by the at least one of the thermal sensors is outside a preset acceptable range of temperatures.

10. The method according to claim 1, wherein the error distribution map is produced as a two dimensional map and the temperature distribution map is produced as a two dimensional map.

11. The method according to claim 1, wherein the error distribution map is produced as a three dimensional map and the temperature distribution map is produced as a three dimensional map.

12. A computer implemented method, comprising:
acquiring signals, indicative of respective metrics at respective locations in a biological tissue, from at least one sensor mounted on a probe in proximity with the biological tissue; and
performing, by a processor, the steps of:
interpolating between the respective metrics determined from the signals so as to produce a metric distribution map;
displaying the metric distribution map on a screen;
determining that at least one of the signals is indicative of an incorrect metric value, and that remaining signals are indicative of correct metric values;
assigning the incorrect metric value of the at least one of the signals a first arbitrary metric value and each correct metric value of the remaining signals a second arbitrary metric value;
interpolating between the first and second arbitrary metric values so as to produce an error distribution map indicative of an error region of the metric distribution map; and
superimposing graphically the error distribution map on the metric distribution map displayed on the screen so as to indicate the error region on the screen during a procedure for treating the biological tissue with the probe.

13. The method according to claim 12, wherein acquiring signals includes acquiring signals from at least one sensor mounted on a probe in proximity with a heart, and wherein the metric comprises a local activation time of the heart.

14. The method according to claim 13, wherein the error distribution map is produced as a three dimensional map and the metric distribution map is produced as a three-dimensional map.

15. The method according to claim 12, wherein the incorrect metric value conflicts with an expected metric value determined in response to the correct metric values.

16. The method according to claim 12, wherein the at least one of the signals provides insufficient information for determining the correct metric value.

17. A computer implemented method, comprising:
acquiring signals, indicative of temperatures at respective locations in a biological tissue, from a plurality of thermal sensors mounted on a probe in contact with the biological tissue; and
performing, by a processor, the steps of:
extrapolating between temperatures determined from the signals so as to produce a temperature distribution map;
displaying the temperature distribution map on a screen;
determining that there is at least one malfunctioning thermal sensor of the plurality of thermal sensors, and that remaining thermal sensors of the plurality of thermal sensors are correctly operating thermal sensors;
assigning the at least one malfunctioning thermal sensor a first arbitrary temperature and each of the correctly operating thermal sensors a second arbitrary temperature;
extrapolating between the first and second arbitrary temperatures so as to produce an error distribution map indicative of an error region of the temperature distribution map; and
superimposing graphically the error distribution map on the temperature distribution map displayed on the screen so as to indicate the error region on the screen during a procedure for treating the biological tissue with the probe.

* * * * *